United States Patent [19]
Fischell et al.

[11] Patent Number: 5,792,172
[45] Date of Patent: Aug. 11, 1998

[54] MULTIFOLD BALLOON FOR STENT DEPLOYMENT

[75] Inventors: Robert E. Fischell, Dayton, Md.; David R. Fischell, Fair Haven, N.J.

[73] Assignee: IsoStent, Inc., Belmont, Calif.

[21] Appl. No.: 774,131

[22] Filed: Dec. 23, 1996

[51] Int. Cl.⁶ .................................................. A61M 29/00
[52] U.S. Cl. ............................................. 606/198; 606/194
[58] Field of Search ........................ 604/96–104; 606/1, 606/108, 192–200; 600/201, 204, 207; 623/1, 11, 12

[56] References Cited

U.S. PATENT DOCUMENTS 4,941,877   7/1990   Montano ........................... 606/194
5,593,412   1/1997   Martinez et al. ................. 606/194

Primary Examiner—Glenn K. Dawson

[57] ABSTRACT

The present invention utilizes a balloon with three or more folds to more evenly distribute the frictional forces on the inside of a stent during stent deployment thus improving the uniformity of stent cell expansion. Ideally one would like to have the same number of balloon folds as the number of stent cells distributed circumferentially around the stent. Matching the number of balloon folds to the number of cells of each cylindrical segment of the stent provides better size uniformity for the stent cells after they are expanded against the wall or other vessel within a human body.

15 Claims, 4 Drawing Sheets

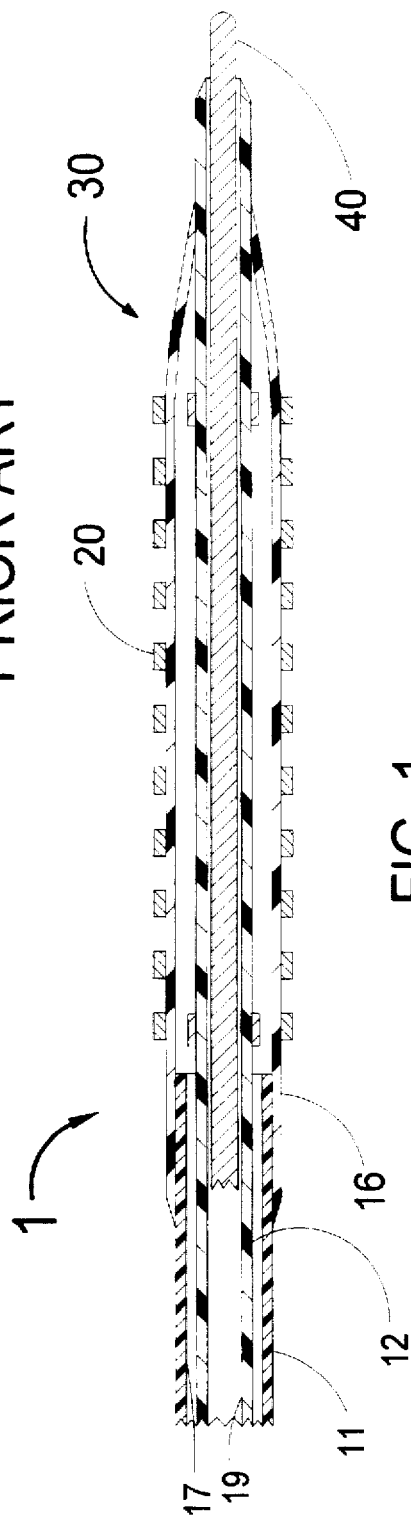
FIG. 1 "PRIOR ART"
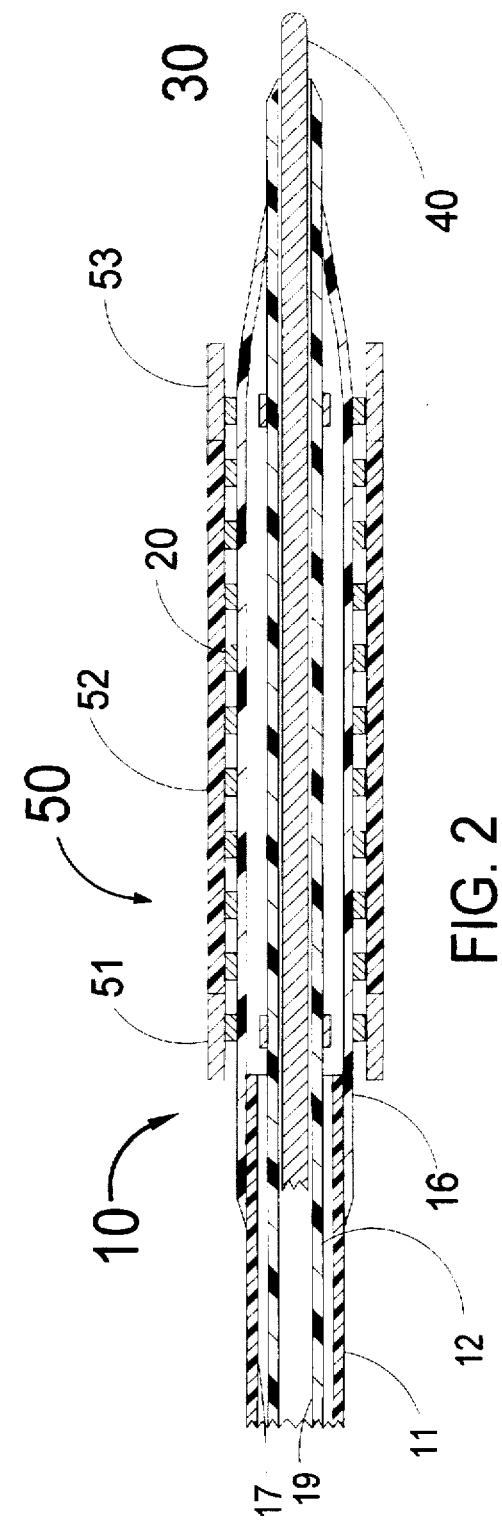
FIG. 2

1

MULTIFOLD BALLOON FOR STENT DEPLOYMENT

FIELD OF USE

This invention is generally in the field of devices for opening vessels of the human body with specific application to percutaneous transluminal coronary angioplasty (PTCA) and stent delivery into a dilated artery.

BACKGROUND OF THE INVENTION

It is well known to use balloon angioplasty catheters for the dilatation of various vessels of the human body and most particularly for opening arteries. It is also well known to place stents into vessels to maintain patency of that vessel. It is also well known to use a balloon catheter for imbedding a stent into the wall of the vessel to maintain vessel patency.

Typical angioplasty balloons are made from non-compliant or semi-compliant plastic which is folded over itself to minimize the catheter cross sectional area during introduction into a patient. These balloons typically have two folds which allow the relatively inelastic plastic of the balloon to be wrapped tightly. During stent delivery, a two-fold balloon applies non-uniform frictional forces to the inside surface of the stent. This can cause a stent which typically has 5 to 9 cells circumferentially disposed in each cylindrical segment of the stent to have some cells expand to a larger size as compared to some other cells. The result of such frictional forces is often seen in stent deployments where cells on one side of the stent are expanded more or less than adjacent cells around the stent's circumference.

SUMMARY OF THE INVENTION

The present invention overcomes the disadvantages of prior art devices by utilizing a balloon with three or more folds to more evenly distribute the frictional forces on the inside of the stent during stent deployment thus improving the uniformity of stent cell expansion.

Ideally one would like to have the same number of balloon folds as the number of stent cells distributed circumferentially around the stent. Twice or half the number of balloon folds as compared to the number of stent cells may also be advantageous.

Although this invention could be used for any vessel of the human body including but not limited to arteries, veins, vascular grafts, biliary ducts, urethras, fallopian tubes, bronchial tubes, etc., the descriptions herein are particularly valuable for coronary artery stenting.

Thus the object of this invention is to improve the uniformity of stent cell expansion during deployment by utilizing a stent delivery balloon with three or more folds.

Another object of this invention is to have the same number of balloon folds as the number of circumferentially distributed stent cells.

Yet another object of this invention is to have exactly twice the number of balloon folds as the number of circumferentially distributed stent cells.

Still another object of this invention is to have exactly half the number of balloon folds as the number of circumferentially distributed stent cells.

These and other objects and advantages of this invention will become apparent to a person of ordinary skill in this art upon careful reading of the detailed description of this invention including the drawings as presented herein.

BRIEF DESCRIPTION OF THE DRAWING

FIG. 1 is a longitudinal cross section of a distal portion of a prior art balloon angioplasty catheter used for stent deployment.

FIG. 2 is an enlarged transverse cross section of the prior art balloon angioplasty catheter at section 2—2 of FIG. 1.

DETAILED DESCRIPTION OF THE INVENTION

Figures 3, 4:
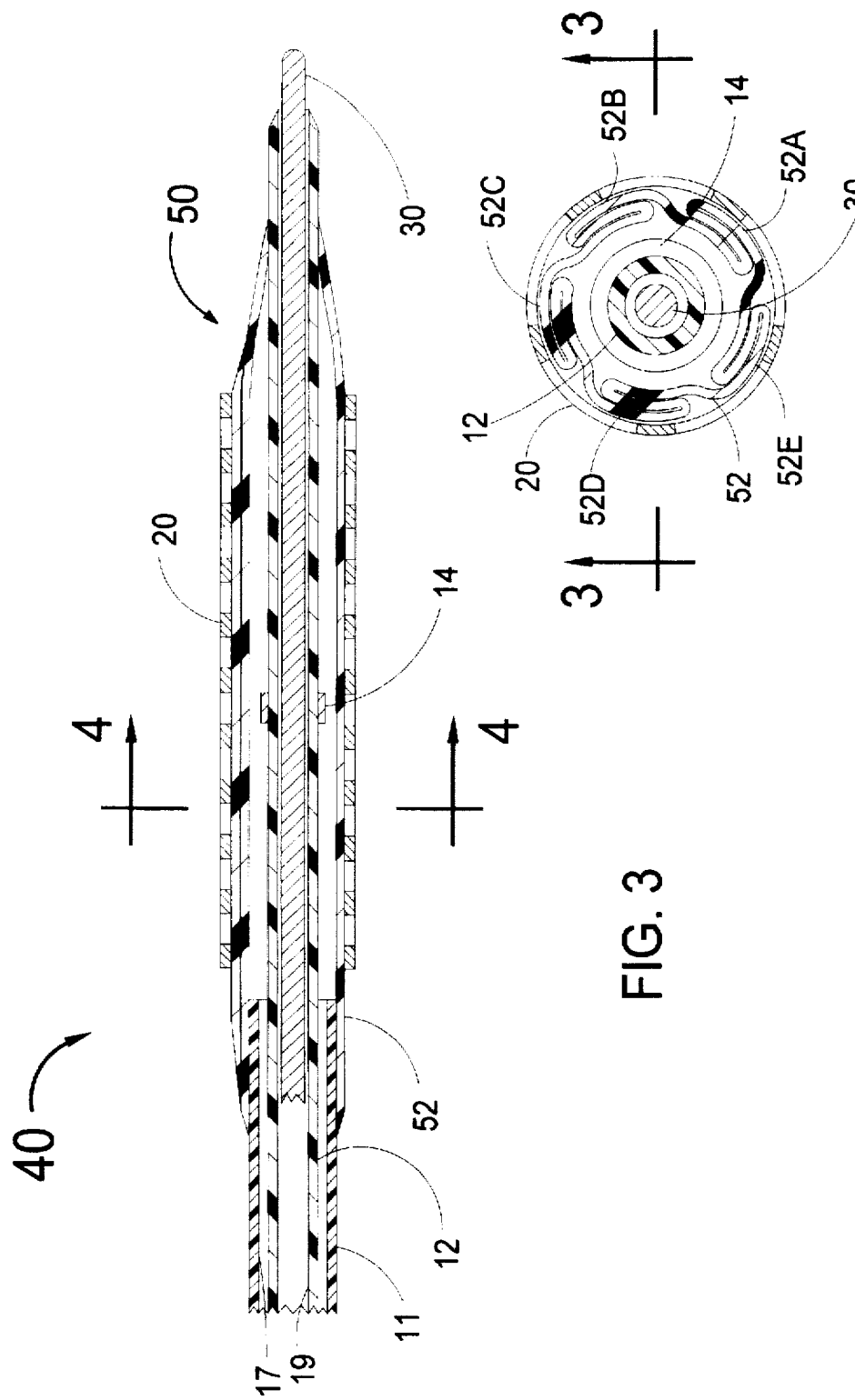
FIG. 3 is longitudinal cross section of a distal portion of a multifold balloon stent delivery catheter.
FIG. 4 is an enlarged transverse cross section of the catheter at section 4—4 of FIG. 3.

U.S. Pat. Ser. No. 4,733,665 by Julio C. Palmaz (which is included herein by reference) describes the expansion of a stent by an angioplasty balloon. U.S. patent application Ser. No. 08/061,562 entitled "Multi-Cell Stent with Cells Having Differing Characteristics" (which application is included herein by reference) describes a stent which has at least three cells disposed circumferentially in each cylindrical segment of which the stent is composed.

FIG. 1 shows a longitudinal cross section of a distal portion of a typical angioplasty balloon stent delivery catheter 10 which includes a stent 20 and a balloon angioplasty catheter 15. Near the distal end of the balloon angioplasty catheter 15 is the angioplasty balloon 16 with folds 16A and 16B (see FIG. 2). The balloon 16 is attached at its proximal end to the distal end of the tube 11 and the distal end of the balloon 16 is joined to the distal end of the inner shaft 12 which has a inner guide wire lumen 19 through which the guide wire 30 can move slideably. The annular passageway 17 between the tube 11 and the inner shaft 12 is in fluid communication with the space between the balloon 16 and the inner shaft 12 and is used to inflate and deflate the balloon 16 so as to expand the stent 20 into the wall of a vessel of the human body. A radiopaque marker band 14 fixed to the inner shaft 12 provides a reference for identifying the center position of the balloon and stent.

FIG. 2 is an enlarged transverse cross section of the catheter 10 at section 2—2 of FIG. 1. The two balloon folds 16A and 16B of the balloon 16 are clearly shown. During expansion of the balloon 16, the folds 16A and 16B and other surfaces of the balloon 16 will exert unequal frictional forces against the inside surface of the stent 20 which may cause the five-cell stent 20 to expand non-uniformly. The number of cells disposed circumferentially in a single cylindrical segment of a stent is clearly defined in the cited U.S. patent application Ser. No. 08/661,562. Between three and nine cells per cylindrical segment is typical for a multi-cell stent. Each cell is formed from a series of wire-like struts that are connected together to form a closed perimeter cell.

To provide more uniformity of expansion of each cell in a cylindrical segment of the stent, it would therefore be highly desirable to have a stent delivery balloon with more than two folds.

FIG. 3 is longitudinal cross section of a distal portion of a multifold balloon stent delivery catheter 40 which includes a stent 20 and a multifold balloon angioplasty catheter 50. Near the distal end of the multifold balloon angioplasty catheter 50, the angioplasty balloon 52 with folds 52A, 52B, 52C, 52D, and 52E (see FIG. 4) is attached at its proximal end to the tube 11 and at its distal end to the inner shaft 12 which has a central guide wire lumen 19 through which the guide wire 30 can move slideably. The annular space 17 between the tube 11 and the inner shaft 12 is in fluid communication with the space between the balloon 52 and the inner shaft 12 and is used to inflate and deflate the balloon 52 so as to expand the stent 20 into the wall of a vessel of the human body. A radiopaque marker band 14 fixed to the inner shaft 12 provides a reference for identifying the position of the balloon 52 and stent 20.

FIG. 4 is an enlarged transverse cross section of the catheter 40 at section 4—4 of FIG. 3. The five balloon folds 52A, 52B, 52C, 52D, and 52E of the balloon 52 are clearly shown. During expansion of the balloon 52, the folds 52A, 52B, 52C, 52D, and 52E will tend to exert essentially equal frictional forces against the inside surface of each of the five cells around the circumference of the stent 20 which will cause the stent 20 to expand more uniformly as compared to a balloon that has only two folds.

Figure 5:
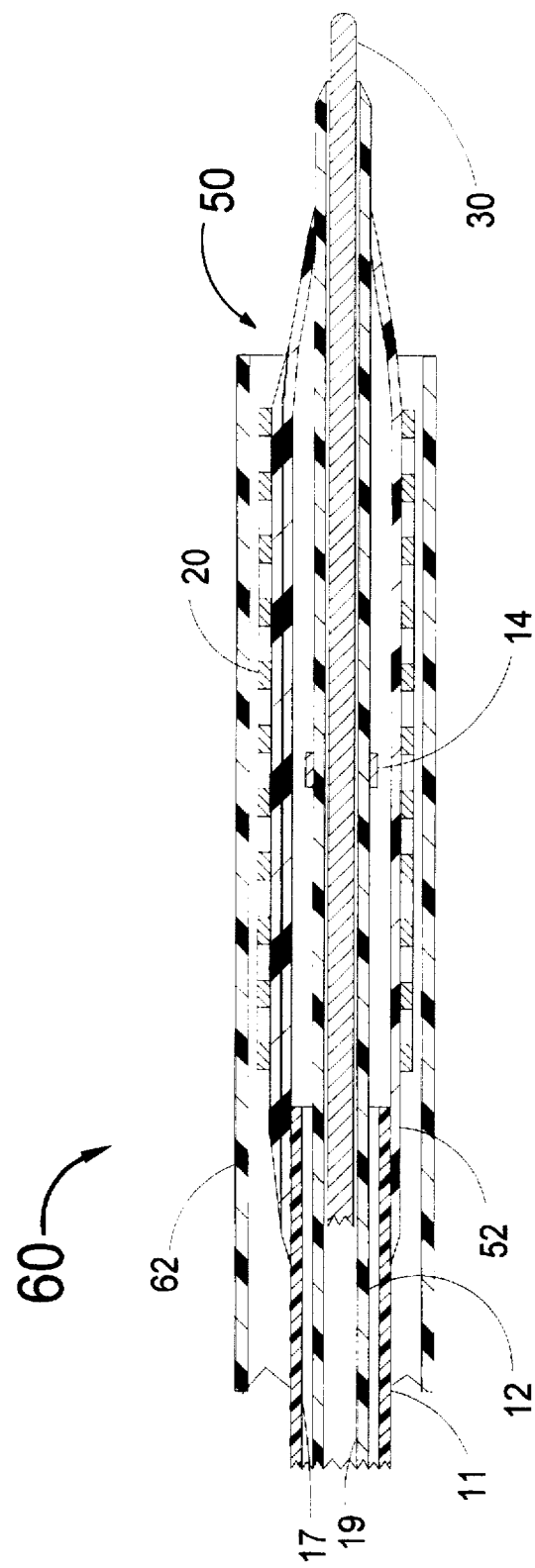
FIG. 5 is a longitudinal cross section of a distal portion of a multifold balloon stent delivery catheter which incorporates a protective sheath.

FIG. 5 is a longitudinal cross section of a distal portion of a multifold balloon stent delivery catheter 60 which incorporates a protective sheath 62 over the angioplasty balloon stent delivery catheter 50 which is identical to that shown in FIGS. 3 and 4. The sheath 62 lies outside of the tube 11 and can be moved slideably with respect to the tube 11 by means located at the proximal end (not shown) of the catheter 60. For a typical stent delivery procedure, the catheter 60 would be advanced with the sheath 62 covering the stent 20 as shown in FIG. 5 until the desired stent placement location is reached. The sheath 62 would then be moved proximally to uncover the stent 20. The balloon 52 would then be inflated to expand the stent 20 against the vessel wall.

It should be understood that the catheters shown in FIGS. 1, 2, 3 and 4 are all shown with each balloon in its compressed state prior to stent deployment. For stent deployment, the balloon is inflated to a pressure that typically is in the range of 3 to 20 atmospheres.

The catheters shown in FIGS. 1, 2, 3 and 4 can be of either the "over-the-wire" type or a "rapid exchange" type both of which are well known in the art of balloon angioplasty. The "over-the-wire type of balloon catheter is characterized by having the central lumen 19 extend for the entire length of the catheter from an entry port (not shown) located at the catheter's proximal end to an exit port at the distal end of the catheter, which exit port is shown in FIGS. 1 and 3. A "rapid exchange" balloon catheter has a guide wire lumen entry port that is situated in a distal half-length of the catheter but proximal to the proximal end of the inflatable balloon.

Figure 6:
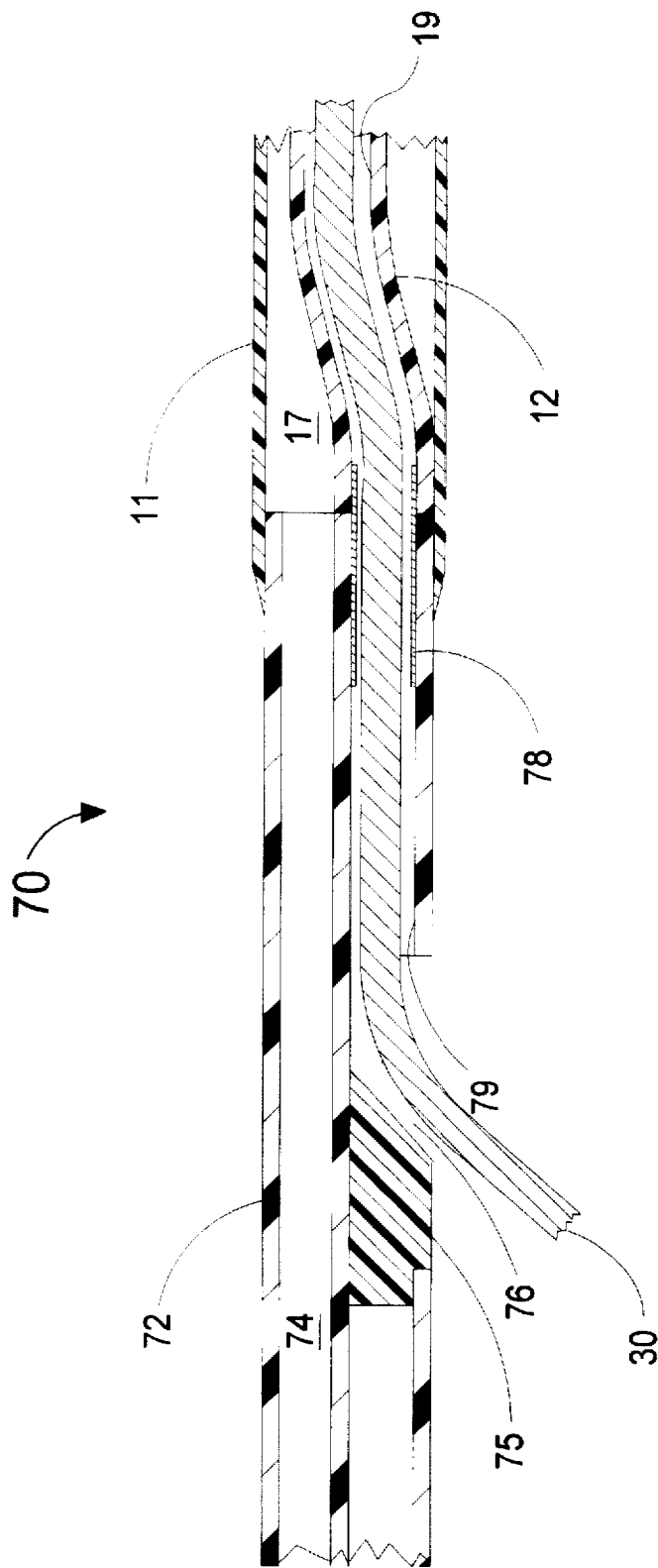
FIG. 6 is a longitudinal cross section of a rapid exchange version of the multifold balloon catheter just proximal to the distal portion where the multifold balloon is located.

An alternative embodiment of the present invention utilizes a rapid exchange concept for the balloon catheter. FIG. 6 shows a longitudinal cross section of a portion of the rapid exchange (as opposed to "over-the wire") multifold balloon stent delivery catheter 70 which portion is located just proximal to the multifold balloon 52. The catheter 70 has a dual lumen tube 72 having a balloon inflate/deflate lumen 74 and a second lumen 79 which is blocked near its distal end by the plug 75. The distal end of the lumen 74 enters into an annular passageway 17 which is in fluid communication with the interior of an inflatable angioplasty balloon as illustrated in FIG. 3. The dual lumen tube 72 is joined at its distal end to the proximal end of the outer cylindrical tube 11 which encloses the annular passageway 17. A thin-walled steel tube 78 can be inserted into the distal end of the lumen 79 at the distal end of the dual lumen tube 72 as a reinforcement. The tube 78 forms a fluid tight connection between the distal end of the lumen 79 and the proximal end of the guide wire lumen 19 inside of the inner shaft 12. An entry port 76 allows the guide wire 30 to enter the lumen 79.

The material(s) selected for the tubes 11, 12, 62 and 72 can be Teflon or an elastomer such as polyurethane or polyethylene. The length of the catheters 10, 40, 60, or 70 is typically 20 to 150 cm depending on the vessel into which it is to be used. The diameter of the catheter will typically vary from 1.0 to 3.0 mm depending on its use. The marker band 14 is typically made from a dense metal such as an alloy of tantalum, platinum or gold.

The fluid entry means at the proximal end of over-the-wire or rapid exchange types of catheters is well known in the art of balloon angioplasty catheters. The method for joining the proximal end of the outer sheath 60 to the exterior surface of the dual lumen tube 72 by means of a Tuohy-Borst fitting is also well known in the art of balloon angioplasty catheter.

It should also be understood that the invention described herein can be used with a variety of angioplasty balloon catheters including those with fixed guide wires at their distal end.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A balloon angioplasty catheter having a distal section and having an inflatable multifold balloon situated at the catheter's distal section, the multifold balloon having a thin wall formed from a plastic material, the balloon having at its longitudinal center at least three folds when in a compressed state prior to balloon inflation with each fold consisting of folding of the balloon's thin wall first in one direction and then the opposite direction so that each one of the at least three folds consists of three layers of the thin wall of the balloon.

2. The catheter of claim 1 wherein the balloon angioplasty catheter has a central lumen throughout its entire length, the balloon angioplasty catheter being of the "over-the-wire" design.

3. The catheter of claim 1 wherein the balloon angioplasty catheter has a distal half-length, the balloon angioplasty catheter being a "rapid exchange" design characterized by having an entry port for a guide wire situated within the distal half-length of the balloon angioplasty catheter.

4. A multifold balloon stent delivery catheter comprising;

a balloon angioplasty catheter having a distal section and having an inflatable multifold balloon situated at the catheter's distal section, the multifold balloon having a thin wall formed from a plastic material, the balloon having at its longitudinal center at least three folds when in a compressed state prior to balloon inflation with each fold consisting of folding of the balloon's thin wall first in one direction and then the opposite direction so that each one of the at least three folds consists of three layers of the thin wall of the balloon; and, a stent placed onto the multifold balloon of the balloon angioplasty catheter, the stent having a multiplicity of cylindrical segments each cylindrical segment consisting of a number of stent cells and the stent further consisting of at least three stent cells circumferentially disposed within each cylindrical segment.

5. The stent delivery catheter of claim 4 wherein the balloon angioplasty catheter has a central lumen throughout its entire length, the balloon angioplasty catheter being of the "over-the-wire" design.

6. The stent delivery catheter of claim 4 wherein the balloon angioplasty catheter has a distal half-length, the balloon angioplasty catheter being a "rapid exchange" design characterized by having an entry port for a guide wire situated within the distal half-length of the balloon angioplasty catheter.

7. The stent delivery catheter of claim 4 including a sheath which covers the stent during catheter introduction into the body, the sheath being adapted to be moved proximally to uncover the stent for stent deployment by balloon expansion.

8. The stent delivery catheter of claim 4 wherein the number of folds of the angioplasty balloon is twice the number of stent cells within one cylindrical segment around the circumference of the stent.

9. The stent delivery catheter of claim 4 wherein the number of folds of the angioplasty balloon is exactly half the number of stent cells within one cylindrical segment around the circumference of the stent.

10. The stent delivery catheter of claim 4 wherein the number of folds of the angioplasty balloon is the same as the number of cells within each cylindrical segment of the stent.

11. The stent delivery catheter of claim 10 wherein there are exactly five folds of the balloon and the stent has exactly five cells circumferentially disposed around each cylindrical segment of the stent.

12. The stent delivery catheter of claim 10 wherein there are exactly six folds of the balloon and the stent has exactly six cells circumferentially disposed around each cylindrical segment of the stent.

13. The stent delivery catheter of claim 10 wherein there are exactly seven folds of the balloon and the stent has exactly seven cells circumferentially disposed around each cylindrical segment of the stent.

14. The stent delivery catheter of claim 10 wherein there are exactly eight folds of the balloon and the stent has exactly eight cells circumferentially disposed around each cylindrical segment of the stent.

15. The stent delivery catheter of claim 10 wherein there are exactly nine folds of the balloon and the stent has exactly nine cells circumferentially disposed around each cylindrical segment of the stent.

* * * * *